United States Patent [19]

Lhonore et al.

[11] 4,260,838

[45] Apr. 7, 1981

[54] PROCESS OF MAKING NITROPARAFFINS BY NITRATION IN THE GASEOUS PHASE

[75] Inventors: Pierre Lhonore, Douai; Jacques Quibel, Maisons Laffitte; Bernard Jacquinot, Douai, all of France

[73] Assignee: Societe Chimique de la Grande Paroisse, Azote et Produits Chimiques, Paris, France

[21] Appl. No.: 25,594

[22] Filed: Mar. 30, 1979

[30] Foreign Application Priority Data

Apr. 4, 1978 [FR] France .............................. 78 09837

[51] Int. Cl.$^3$ ............................................ C07C 76/02
[52] U.S. Cl. .................................................. 568/947
[58] Field of Search .......................... 260/644; 568/947

[56] References Cited

U.S. PATENT DOCUMENTS

| | | | |
|---|---|---|---|
| 2,511,454 | 6/1950 | Bishop et al. | 260/644 |
| 3,113,975 | 12/1963 | Standish et al. | 260/644 |
| 3,133,123 | 5/1964 | Bonfield | 260/644 |
| 3,272,874 | 9/1966 | Abbott | 260/644 |
| 3,378,596 | 4/1968 | Toops, Jr. et al. | 260/644 |
| 3,780,115 | 12/1973 | Lhonore et al. | 260/644 |

FOREIGN PATENT DOCUMENTS

| | | |
|---|---|---|
| 1037438 | 8/1958 | Fed. Rep. of Germany . |
| 2158708 | 6/1973 | France . |

OTHER PUBLICATIONS

Mladenov et al., Chem. Abs., vol. 84, (1976), 16686y.

*Primary Examiner*—Leland A. Sebastian
*Attorney, Agent, or Firm*—Browdy & Neimark

[57] ABSTRACT

Nitroparaffins are made by nitration in the gaseous phase under pressure, possibly in the presence of a gas containing oxygen. The reagent to be nitrated is a mixture containing a substantial amount of propane, the reaction temperature and pressure, the contact time and the quantitative ratios between the nitrating agent, the mixture to be nitrated and the oxygenated gas being selected so that the nitration reaction is conducted in a homogeneous gaseous phase. The process makes it possible to obtain a percentage of different nitroparaffins in response to industrial demand and further to use the cheapest raw materials at a given moment.

12 Claims, 8 Drawing Figures

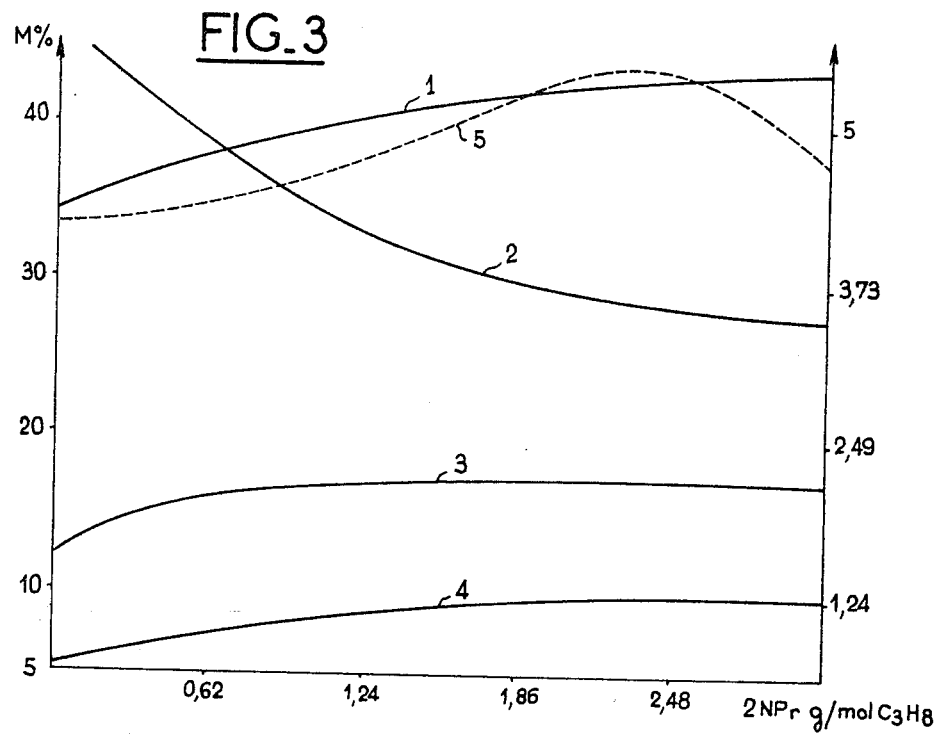
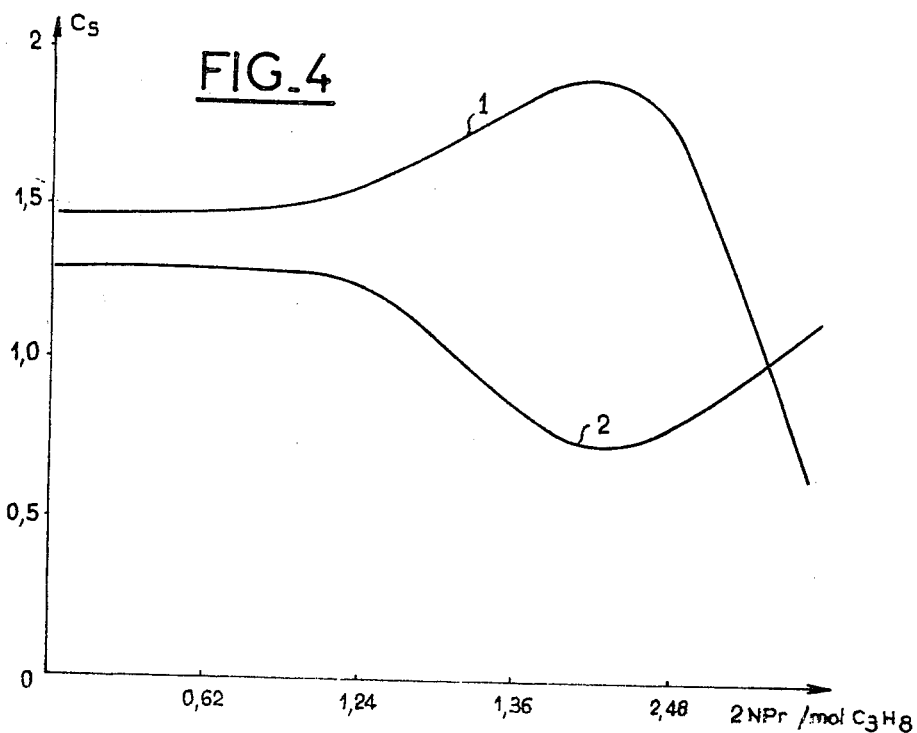

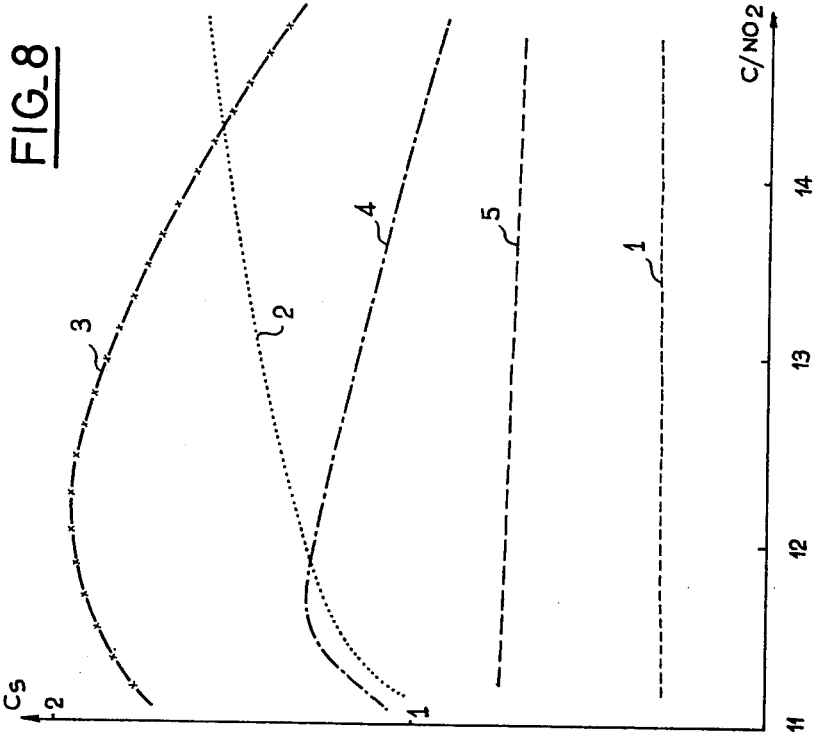
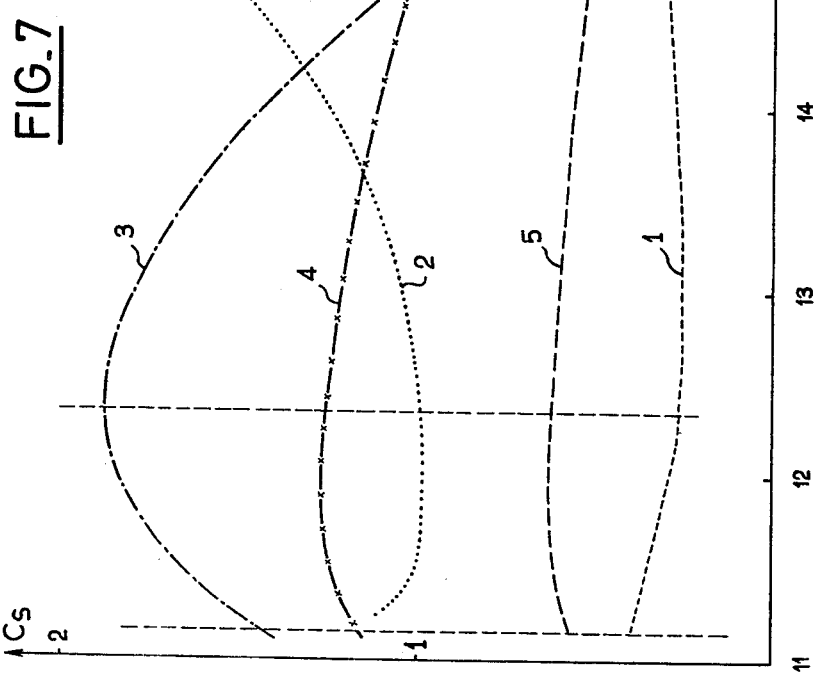

PROCESS OF MAKING NITROPARAFFINS BY NITRATION IN THE GASEOUS PHASE

FIELD OF INVENTION

This invention relates to a process of manufacturing nitroparaffins in a gaseous phase by nitration under pressure.

BACKGROUND OF THE INVENTION

A process has already been proposed in U.S. Pat. Nos. 3,780,115 and 3,869,253 for nitrating a saturated hydrocarbon, such as propane, particularly in the presence of oxygen, introduced in the form of air, wherein the nitration is conducted under a pressure between 8 and 14 bars, the reactant gases being separately preheated under reaction pressure and introduced at between 150° and 330° C. to a reaction zone, the gaseous effluents coming from the nitration zone being subjected to a quenching or rapid cooling. This nitration process leads to an orientation of final products toward nitropropanes with a very clear predominance of 2-nitropropane.

One of the industrial problems resides in the search for means making possible nitration operations to obtain a suitable percentage of different nitroparaffins to meet market requirements. It has now been found that 2-nitropropane does not at present represent the most worthwhile nitroparaffin from the point of view of the industry's need.

Further, an effort is being made to optimize the profitability of nitration of hydrocarbons, particularly in already existing installations, and by the use of the cheapest materials available on the market.

SUMMARY OF THE INVENTION

A process has now been found to manufacture nitroparaffins by nitration in the gaseious phase under pressure, possibly in the presence of a gas containing oxygen, such as air, which makes it possible to meet the above needs. According to this process, the reactant to be nitrated is made up of a mixture containing propane, preferably recycled nitroparaffin and possibly inert gas and/or another alkane; the nitrating agent is nitrogen peroxide or nitric acid, either alone or in mixture, or any other agent carrying an NO or $NO_2$ group that is easily transferable. The reaction temperature and pressure, the contact time and the quantitative ratios between nitrating agent, the mixture containing propane, and possibly the oxygenated gas, are selected so that the nitration is conducted in a homogeneous gaseous phase.

DETAILED DESCRIPTION OF EMBODIMENTS

Figure 2:
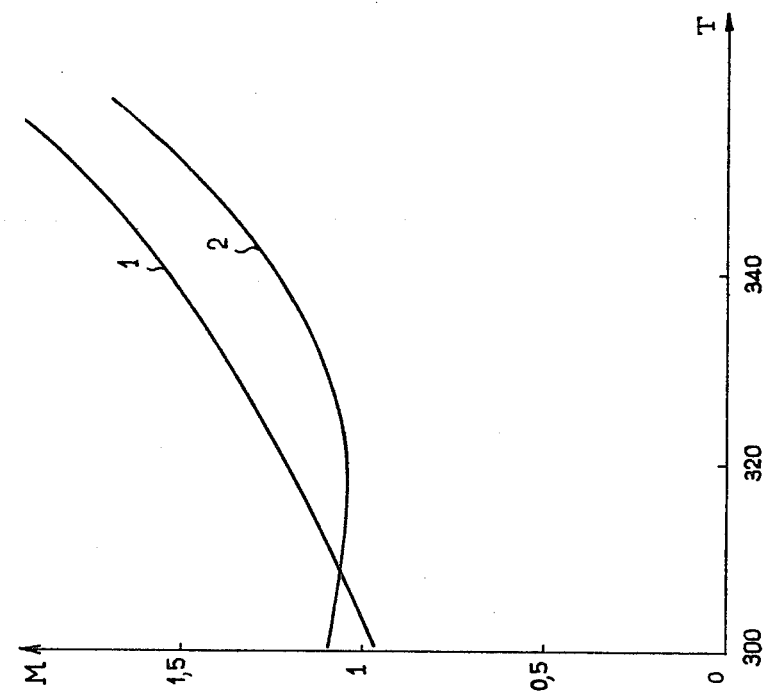

The process can be conducted under different reaction pressures, from atmospheric to 100 bars, preferably between 10 and 30 bars. The reaction contact time can go from 0.01 to 20 seconds, particularly 1 to 10 seconds, preferably on the order of 5 to 8 seconds.

It has been observed with nitric acid and nitrogen peroxide and other nitrating agents as well that the reaction temperature variation makes it possible under certain conditions to change the spectrum of nitroparaffins with a concomitant variation in the specific consumptions of alkane and nitrating agent. The temperature zone to be taken into consideration in using nitrogen peroxide is 280° to 350° C. With nitric acid, it can be higher, on the order of 300° to 500° C.

In the case of nitration of propane with nitrogen peroxide, in the presence of air, an increase of reaction temperature from 300° to 360° C. leads to a variation in the distribution of the nitroparaffins produced corresponding to an increase in the percentage of nitromethane in the condensed effluent and a slight increase in the amount of nitroethane and 1-nitropropane with a simultaneous rapid and considerable drop in the quantity of 2-nitropropane.

Although raising the temperature involves an increase in specific consumption of propane and nitrating agent, there are high temperature operating points for which the profitability of the nitration is maximal, given that 2-nitropropane is less valuable than the other three nitroalkanes. It can be assumed that some of the reaction parameters such as contact time and pressure have an influence which is superposed on that of the temperature.

It has been found that the presence in the mixture to be nitrated of one or more nitroparaffins selected from nitroalkanes, particularly from nitroparaffins made during the nitration, make it possible to reduce the corresponding amount of nitroalkane produced. The interaction of the nitroalkanes introduced during the nitration reaction with the nitroalkanes during formation leads to modifications in the structure of the industrially usable products. In particular, it is possible to recycle nitroparaffins in excess at a given moment, considering the needs of the market, to make other nitroparaffins in a large proportion. The amount of nitroparaffins recycled after separation of the reaction effluents can be between 10 and 100% of the total amount of the nitroparaffins produced. Recycling is sequenced when it involves the totality of nitroparaffins manufactured, with alternating recycling and production.

Addition of 2-nitropropane to the propane starting material constitutes a particular case which leads to a considerable variation in the structure of the nitroalkanes produced corresponding to an increase in the production of nitromethane at the expense of 2-nitropropane. It is further found that when amount of 2-nitropropane is large at the reactor input, with an equivalent amount being removed in the liquid effluent the percentage of 2-nitropropane coming out is less and the amount of nitromethane is greater and those of 1-nitropropane and nitroethane are slightly increased.

Recycling one of the other nitroalkanes also changes the distribution of the end products. It is the same when 2-nitropropane is recycled with one or more other nitroparaffins. Recycling of two, even three or four nitroalkanes changes the spectrum of the finished products.

It has also been found that specific consumption of nitrogen peroxide and propane drops when 2-nitropropane is recycled, this consumption being smaller the greater the amount recycled. Although recycling is an operation that consumes energy, it can cause a gain in the useful consumption of initial materials. Further, the price of some nitroparaffins not being constant on the market, the choice of the products recycled in determined amounts makes it possible to find the maximal profitability of the production unit.

This phenomenon whereby the product consumption is controlled by selective recycling is of the same type regardless of the nitrating agent used. Further, the amounts recycled or introduced in the mixture to be nitrated can be greater than the amounts produced, particularly when there is a reserve of products in storage.

Variations in the reaction heat when alkanes are recycled require temperature regulating systems, permitting either heating of the reactor or cooling it or, alternately, both.

On the other hand, it has been found advantageous to nitrate mixtures containing propane and one or more other alkanes going up to five carbon atoms in the molecule, such as methane, ethane, butane and pentane. Propane-ethane mixtures are particularly advantageous. Addition of ethane to propane subjected to nitration leads to the progressive change of the distribution of the end nitroparaffins. An increase in the amount of ethane in the input mixture causes a reduction of 1-nitropropane and 2-nitropropane. Drop in production of 2-nitropropane and 1-nitropropane is very rapid starting from an ethane/propane weight ration of 2 at the reactor input. On the other hand, a very clear increase of nitroethane production is noted.

Thus, thanks to a selected composition of the mixture to be nitrated of ethane in prelation to propane, it is possible to bring out the spectrum of nitroparaffins meeting the customer's needs. It is possible to consider adding two or three other hydrocarbons to the propane, depending on the distribution of nitroparaffin products desired.

On the other hand, still as a function of the finished products expected, it has been considered advantageous to mix with propane at least one of the compounds present in the aqueous effluent stage, selected from ketones, aldehydes, alcohols, acids, nitriles formed during the nitration reaction, separated and recycled. Also, depending on the case, it can be advantageous for the mixture to be nitrated to contain a compound that can release an $NO_2$ group, a halogen or free radicals, in particular chloronitroparaffins containing from 1 to 4 carbon atoms in the molecule.

It has also been found that the performance of the nitration of mixtures containing propane, particularly ethane-propane and propane-other nitroparaffin mixtures in the presence of inert gases such as nitrogen, carbon monoxide and carbon dioxide is advantageous. The same effects were observed with recycling of a nitroparaffin produced, such as 2-nitropropane, and the recycling of 2-nitropropane in the presence of inert gases is particularly advantageous for producing nitromethane. Under these conditions, a greater influence of the temperature on the production of 2-nitropropane has been noted.

In the presence of inert gases, regardless of the type of mixture with a propane base, it is possible to obtain the same specific consumption as in the absence of inert gases provided the reaction parameters are rigorously chosen. It appears advantageous to perform the nitration of propane-ethane mixtures in the presence of at most 50% by volume of inert gases.

Examples that illustrate the invention in a non-limiting way are given below.

EXAMPLE 1

Influence of reaction temperature variation

Nitration of propane is performed at temperatures of 300°, 320° and 340° C., under a pressure of 10 bars, in the presence of air, the nitrating agent being nitrogen peroxide, for contact periods on the order of 7 seconds. The quantitative ratios at the reactor input between the nitrating agent and propane, air and propane and the are expressed by weight, and the composition of the liquid phase $\phi$ L in weight percentages of nitroparaffins and consumption by weight of propane $C_3H_8c$ and of nitrogen peroxide $NO_2c$ converted to kilogram of totality of nitroparaffins produced NPf.

The test results are given in table 1 below, in which the reaction temperatures T°C. are indicated in degrees centigrade, the reaction times ts are expressed in seconds, the pressure P in bars, the nitrogen peroxide and propane represented by $NO_2$ and $C_3H_8$, the nitroparaffins produced by weight considered overall represented by N P f, nitromethane by NM, nitroethane by NE, 2-nitropropane by 2 NP, 1-nitropropane by 1 NP.

TABLE I

| Test No. | 1 | 2 | 3 |
|---|---|---|---|
| T °C. | 300 | 320 | 340 |
| ts | 7.2 | 7 | 6.8 |
| P | 10 | 10 | 10 |
| $NO_2/C_3H_8$ input | 0.21 | 0.21 | 0.21 |
| Composition $\phi$ L | | | |
| NM | 23 | 29.3 | 34.5 |
| NE | 5.3 | 5.6 | 6.1 |
| 2 NP | 58.1 | 51.4 | 46.6 |
| 1 NP | 13.6 | 13.7 | 12.8 |
| $C_3H_8$ c | 0.96 | 1.08 | 1.95 |
| NP F | | | |
| $NO_2c$ | 1.09 | 0.995 | 1.27 |
| NP f. | | | |
| Air/$C_3H_8$ input | 0.238 | 0.238 | 0.238 |

From reading the table it can be seen that an increase in temperature, under comparable conditions for other parameters, leads to an increase in the amount of nitromethane in the condensed effluent, and concomitantly to a slight increase of nitroethane and 1-nitropropane with a rapid and considerable drop in the amount of 2-nitropropane.

In this case, when the temperature increases, it is noted that the specific consumption of propane increases, reduced to kg of the totality of nitroparaffins produced, and also that of nitrogen peroxide. However, because of the increase in production of nitromethane, nitroethane and 1-nitropropane and their industrial interest, certain relatively high temperature operating points correspond to a maximal efficiency of the nitration operation. The evolution of the spectrum of nitroparaffins produced in the liquid effluent and that of specific consumption of propane and nitrating agent are shown in FIGS. 1 and 2 of the accompanying drawing.

Figure 1:
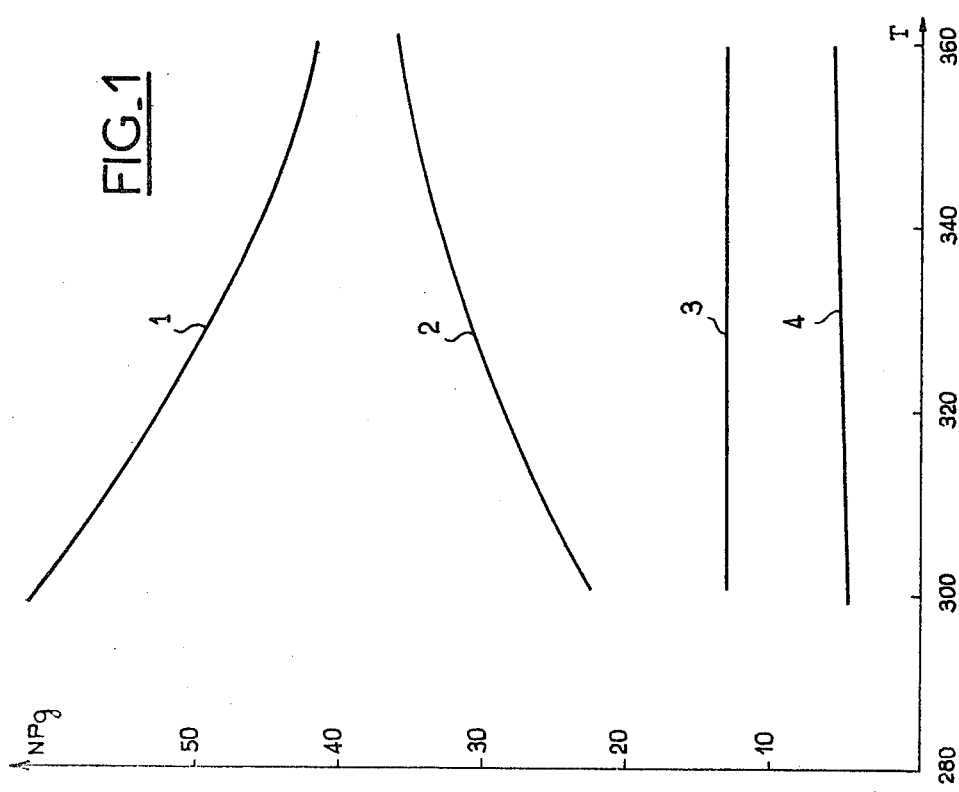

FIG. 1 relates to variations in the compositions expressed in percentages by weight of the nitroparaffins made, Npf, plotted on the ordinates as a function of the reaction temperature expressed in degrees centigrade, T plotted on the abscissas. The 2-nitropropane, 2 NP, corresponds to curve 1; nitromethane, NM, to curve 2; 1-nitropropane, 1 NP, to curve 3; and nitroethane, NE, to curve 4.

FIG. 2 relates to specific consumption in kg per kg of nitroparaffins produced for a propane/nitrogen peroxide ratio of 5 moles and air/nitrogen peroxide of 1.8 moles. On the ordinates are plotted the masses M consumed of propane and nitrogen peroxide in kg per kg of the totality of nitroparaffins produced and on the abscissas the temperatures T in degrees centigrade. Curve 1 corresponds to propane and curve 2 to nitrogen peroxide.

EXAMPLE 2

Recycling of 2-nitropropane

A series of tests were run in which nitration of propane was performed at a reaction temperature of 340° C., under a pressure of 10 bars, with a reaction time of 7 seconds, ratios of the nitrating agent, i.e., nitrogen peroxide/propane at the input by weight and air/propane under the same conditions, respectively, of 0.21 and on the order of 0.24.

The test results are given in table II, in which are shown the ratios by weight at the input of the reactor of recycled 2-nitropropane propane, 2 $NPr/C_3H_8$ input, the composition expressed in percentage by weight of the nitroparaffins in the output liquid phase $\phi$ L, nitromethane NM, nitroethane, NE, 2-nitropropane 2 NP, 1-nitropropane 1 NP, and the composition of the exit liquid phase after removal of the nitropropane to be recycled $\phi$ L-2 NP, and the specific consumption of propane $C_3H_8$ and of nitrogen peroxide $NO_2$c consumed/nitroparaffins produced by weight NP f.

There are 4 test numbers, the comparative test being test 0.

FIG. 3 of the accompanying drawing illustrates the influence of the recycling of 2-nitropropane on the spectrum of nitroparaffins produced.

The mass ratios in grams of recycled 2-nitropropane to moles of propane introduced are plotted on the axis of the abscissas 2 $NPrg/mol$ $C_3H_8$. The mass percentages of each nitropropane M% are plotted on an axis of the ordinates and the mass ratios of the nitroparaffins produced to moles of propane introduced MNPf/mol $C_3H_8$ appear on the other axis of the ordinates.

The influence of recycling 2-nitropropane was studied within the framework of the nitration reaction conducted at 340° C., for a ratio propane/nitrogen peroxide of 5 moles and air/nitrogen peroxide of 1.8.

Curves 1, 2, 3 and 4 correspond respectively to production of nitromethane, 2-nitropropane, 1-nitropropane, nitroethane.

Curve 5, which shows the evolution of the production of the totality of nitroparaffins as a function of the amount of recycled 2-nitropropane shows a maximum. At this point, for the same amount of propane introduced there corresponds a maximal production of the totality of the nitroparaffins and consequently a minimal size installation.

FIG. 4 of the accompanying drawing relates to specific consumptions in kg per kg of the totality of nitroparaffins produced, within the framework of a nitration reaction of propane conducted at 340° C., for a ratio propane/nitrogen peroxide of 5 moles and air/nitrogen peroxide of 1.8.

Specific consumptions Cs of propane and nitrogen peroxide are plotted on the ordinates and the mass ratios of recycled 2-nitropropane/moles of $C_3H_8$ introduced 2 NPr/mol $C_3H_8$ on the abscissas. Curve 1 corresponds to propane and curve 2 to nitrogen peroxide.

TABLE II

| Test No | 0 | 1 | 2 | 3 | 4 |
|---|---|---|---|---|---|
| T °C. | 340 | 340 | 340 | 340 | 340 |
| ts | 7 | 7 | 7 | 7 | 7 |
| P | 10 | 10 | 10 | 10 | 10 |
| $NO_2/C_3H_8$ input | 0.21 | 0.21 | 0.21 | 0.21 | 0.21 |
| Air/$C_3H_8$ input | 0.238 | 0.238 | 0.238 | 0.240 | 0.240 |
| 2 NPr/$C_3H_8$ input | 0 | 0.070 | 0.0224 | 0.056 | 0.058 |
| Composition % $\phi$ L | | | | | |
| NM | 34 | 26.6 | 32 | 29.5 | 27.5 |
| NE | 6 | 6.3 | 7.3 | 7.5 | 6.3 |
| 2 NP | 47 | 56.1 | 47 | 51 | 55.2 |
| 1 NP | 13 | 11 | 13.7 | 12 | 11 |
| Composition % $\phi$ L-2NP | | | | | |
| NM | 34 | 44 | 39.3 | 43 | 40 |
| NE | 6 | 10 | 8.7 | 11 | 9 |
| 2 NP | 47 | 28 | 35.2 | 29 | 35 |
| 1 NP | 13 | 18 | 16.8 | 17 | 16 |
| $C_3H_8$ c NP f | 1.95 | 0.82 | 1.42 | 1.83 | 1.42 |
| $NO_2$ c NP f | 1.27 | 1.070 | 1.28 | 0.80 | 0.70 |

From reading table II and FIG. 3 it can be deduced that the greater the amount of 2-nitropropane at the reactor input, an equivalent amount having been removed in the effluent liquid phase, the lower the percentage of 2-nitropropane produced, while that of nitromethane is higher and those of 1-nitropropane and nitroethane increase slightly. In this case, the temperature variation in the structure of the nitroparaffins produced is represented essentially by an increase of the nitromethane at the expense of the 2-nitropropane.

Going from the curves of FIG. 4, it will be noted that the consumption of nitrogen peroxide and propane drops when 2-nitropropane is recycled, this consumption being smaller the greater the amount of 2-nitropropane.

EXAMPLE 3

Nitration of ethane-propane mixtures

A series of tests were run of nitration of propane in the presence of ethane, at reaction temperatures from 320° to 340° C., under a pressure of 10 bars, with a reaction time of 5.5 seconds and nitrating agent ratio: nitrogen peroxide/hydrocarbons $C_2H_6+C_3H_8$ at the reactor input (designated by CHs) on the order of 0.2. The number of tests was 8, the comparative test being test 0.

The test results are given in table III, in which appear the ratios $NO_2/CHs$ (nitrogen peroxide to the total of hydrocarbons) by weight at the reactor input, also for air/CHs by weight, then $C_2H_6/C_3H_8$ by weight at the reactor input. The table also contains the composition of the liquid phase in percentage by weight % $\phi$ L of nitromethane NM, nitroethane NE, 2-nitropropane 2 NP and 1-nitropropane 1 NP, and noting of the specific consumption for ethane, propane, ethane+propane and nitrogen peroxide in relation to the totality of nitroparaffins produced.

TABLE III

| Test No | 0 | 1 | 2 | 3 | 4 | 5 | 6 | 7 |
|---|---|---|---|---|---|---|---|---|
| T °C. | 340 | 340 | 340 | 340 | 340 | 320 | 340 | 320 |
| ts | 5.5 | 5.5 | 5.5 | 5.5 | 5.5 | 5.5 | 5.5 | 5.5 |
| P | 10 | 10 | 10 | 10 | 10 | 10 | 10 | 10 |
| $NO_2/CH$ s | 0.21 | 0.20 | 0.20 | 0.20 | 0.20 | 0.20 | 0.20 | 0.20 |
| Air/CH s | 0.238 | 0.053 | 0.053 | 0.048 | 0.05 | 0.05 | 0.05 | 0.050 |
| $C_2H_6/C_3H_8$ | 0 | 1 | 1.04 | 1.02 | 2 | 2 | 4 | 4 |
| Composition % $\phi$ L | | | | | | | | |
| NM | 34.5 | 29.7 | 32.8 | 31.5 | 34.0 | 27 | 31.7 | 26.5 |
| NE | 6.1 | 17.6 | 17.1 | 17.7 | 23.5 | 25.4 | 35.5 | 37.3 |
| 2 NP | 46.6 | 38 | 37.9 | 39 | 32.5 | 37.2 | 24.5 | 28.5 |
| 1 NP | 12.8 | 14.7 | 12.2 | 12.8 | 10 | 10.3 | 8.3 | 7.6 |
| $C_2H_6$ c/NPf | | 0.17 | 0.57 | 0.68 | 0.60 | 0.45 | 0.132 | 0.85 |
| $C_3H_8$ c/NPf | | 0.32 | 0.81 | 0.59 | 0.45 | 0.39 | 0.11 | 0.36 |
| $C_2H_6$c + | 1.95 | 0.49 | 1.38 | 1.27 | 1.05 | 0.84 | 1.43 | 1.21 |

TABLE III-continued

| Test No | 0 | 1 | 2 | 3 | 4 | 5 | 6 | 7 |
|---|---|---|---|---|---|---|---|---|
| C₃H₈c | | | | | | | | |
| NPf | | | | | | | | |
| NO₂ c/NPf | 1.27 | 0.9 | 0.9 | 1.18 | 1.41 | 0.89 | 1.37 | 1.12 |

Figure 5:
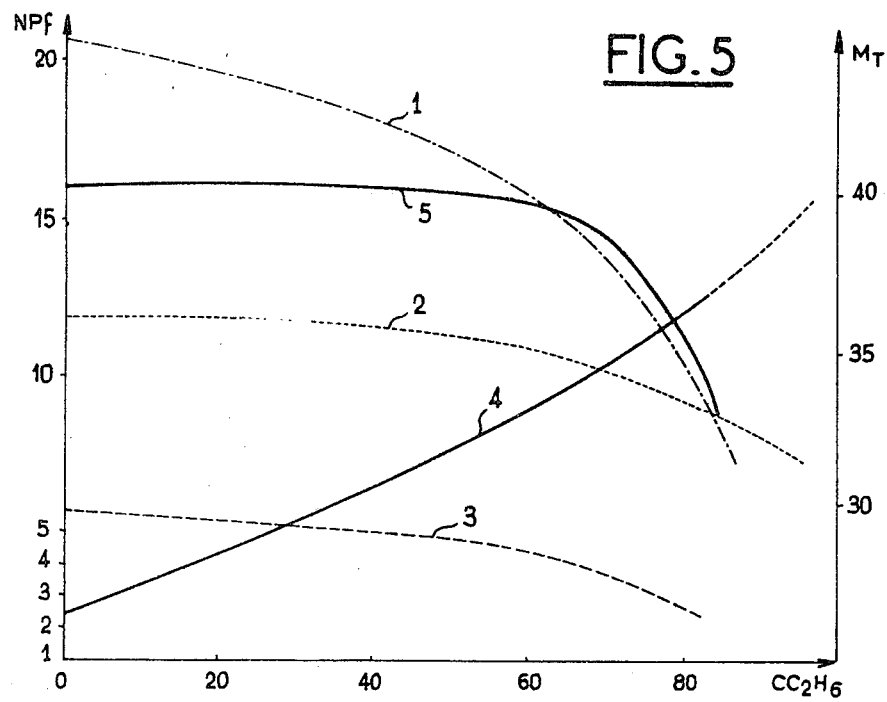

FIG. 5 of the accompanying drawing shows the evolution of the mass of various nitroparaffins produced and that of the totality of the mass as a function of the ratio ethane/propane in the mixture to be nitrated. The masses produced in grams for each nitroparaffin are plotted on an axis of the ordinates NPf and the total mass of nitroparaffins produced in grams MT is plotted on a second axis of the ordinates. Curves 1, 2, 3 and 4 correspond respectively to 2-nitropropane, nitromethane, 1-nitropropane and nitroethane. Curve 5 corresponds to the evolution of the total mass produced in grams.

Figure 6:
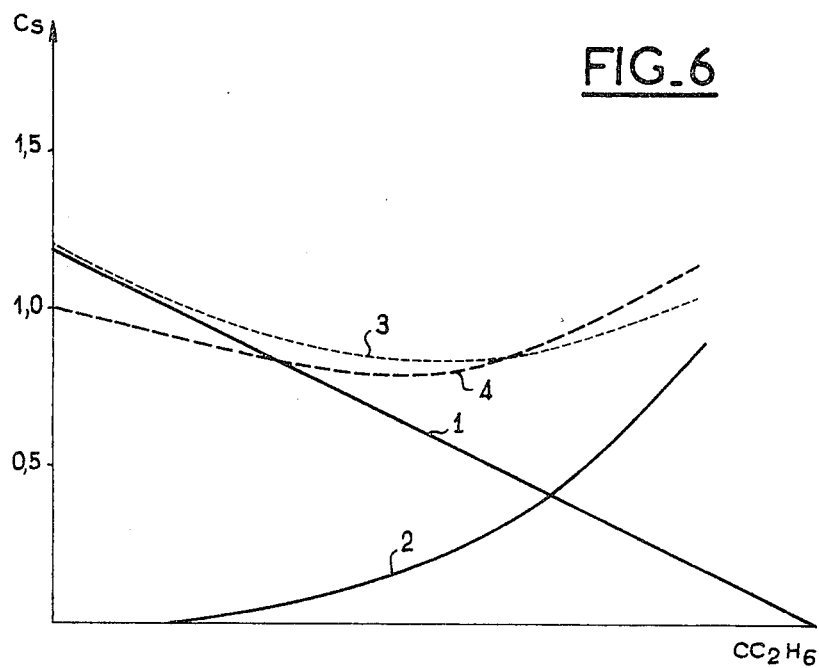

FIG. 6 of the accompanying drawing represents the variations in specific consumption in kg per kg of nitroparaffins produced as a function of the ratio ethane/propane at the reactor input. The specific consumptions kg/kg Cs are plotted on the ordinates and the percentages of carbons introduced in the form of ethane C $C_2H_6$ appear on the axis of the abscissas. Curves 1, 2, 3 and 4 correspond respectively to the consumption of propane, ethane, sume of ethane+propane and of nitrogen peroxide.

From reading table III and from the curves of FIGS. 5 and 6 it can be seen that the amounts of ehtane introduced in the mixture to be nitrated constitute a means of regulating the spectrum of nitroparaffins produced. When the percentage of ethane increases in the mixture, the amount of 2-nitropropane decreases, and also that of 1-nitropropane. Production of 2-nitropropane changes very rapidly starting from the ratio $C_2H_6/C_3H_8$ by weight equal to 2. On the other hand, a very clear increase of the production of nitroethane is noted. By choosing the composition of the starting mixture to be nitrated, the desired nitroparaffin is produced. Further, it will be noted that overall the specific consumptions are less with the mixture than for the propane alone. When ethane and propane are mixed, more of all the finished products are obtained than when using only one of the two hydrocarbons; i.e., the total yield is greater.

EXAMPLE 4

Nitration of ethane-propane mixtures in the presence of inert gases

A series of tests were run of nitrating 50/50 ethane-propane mixtures in the presence of carbon dioxide. The nitrating agent was nitrogen peroxide. The reaction temperatures T°C. were between 325° and 330° C. The reaction times ts were between 7.9 and 8.2 seconds. The nitration pressure was 10 bars. The $CO_2$ was present at a rate of 40% by volume. The molar rations CHs/air, i.e., ratios of the sum of hydrocarbons to air, were between 49 and 67. The proportions of hydrocarbons are expressed in percentages of gram-atoms of carbon, i.e., 50% of the carbons come from ethane and 50% from propane.

FIG. 7 of the accompanying drawing show the influence of the ratio C (gram-atoms) to $NO_2$ in moles on nitration of a propane-ethane mixture in the presence of inert $CO_2$. Variations of specific consumptions Cs, i.e. kg per kg of nitroparaffins produced, are plotted on the ordinates and the ratio C (gram-atom)/NO₂(mole)C/NO₂ on the abscissas. Curve 1 corresponds to the specific consumption of ethane, curve 2 to the specific consumption of propane, curve 3 to the specific consumption of nitrogen peroxide $NO_2$, curve 4 to the total production of nitroparaffins, curve 5 to the amount of nitromethane produced expressed in grams per 100 gram-atoms of carbon.

From a reading of the curves it will be noted that the consumption of $NO_2$ shows a maximum for the ratio hydrocarbons/NO₂mol 12.4 and at a nitration temperature of 325° C., propane consumption being minimal.

Another series of tests were run with the same mixture of ethane-propane (CHs) % carbons in ethane 50 and propane 50, in the presence of $CO_2$ 40% volume, the ratios (C/O₂) mol being between 49 and 67, the reaction time 7.9 to 8.1 seconds, at nitration temperatures between 323° and 326° C. The reaction was conducted in the presence of recycled 2-nitropropane (2 NPr/CHs) mol. 0.009 to 0.011.

FIG. 8 of the accompanying drawing shows the influence of the ratio C (gram-atoms) to $NO_2$ in moles on nitration of propane-ethane mixtures in the presence of an inert gas ($CO_2$) and recycled 2-nitropropane. Curve 1 corresponds to the specific consumption of ethane, curve 2 to the specific consumption of propane, curve 3 to the specific consumption of $NO_2$, curve 4 to the total production of nitroparaffins and curve 5 to the amount of nitromethane produced expressed in grams per 100 gram-atoms of carbon. Specific consumption CS (kg per kg of nitroparaffins produced) are plotted on the ordinate and the ratios C/NO₂ on the abscissas.

The same effects as above and the advantage of recycling 2-nitropropane for production of nitromethane were observed.

It will be obvious to those skilled in the art that various changes may be made without departing from the scope of the invention and the invention is not to be considered limited to what is shown in the drawings and described in the specification.

We claim:

1. In a process of manufacturing nitroparaffins by nitration in homogeneous gaseous phase under pressure of at least one hydrocarbon, wherein the reactant hydrocarbon to be nitrated comprises propane which is introducted into a reaction zone, the nitrating agent being nitrogen peroxide, nitric acid, alone or in mixture or any agent carrying an easily transferable NO or $NO_2$ group, the improvement wherein said homogeneous gaseous phase subjected to nitration further comprises at least one nitroparaffin including 2-nitropropane, whereby a mixture of propane and 2-nitropropane is introduced into the reaction zone.

2. Process of manufacturing nitroparaffins according to claim 1 wherein the reaction temperature is between 280° and 350° C. and the nitrating agent is nitrogen peroxide.

3. Process of manufacturing nitroparaffins according to claim 1 wherein the nitroparaffins introduced to the reaction mixture are separated from the reaction effluents and recycled, the amount of recycled nitroparaffins representing 10 to 100% of the total amount of nitroparaffins produced.

4. Process of manufacturing nitroparaffins according to claim 3 wherein the recycling is sequenced when it involves the totality of nitroparaffins produced, with alternating of recycling and production of nitroparaffins.

5. Process of manufacturing nitroparaffins according to claim 1 wherein the mixture to be nitrated contains propane and one or more other alkanes of up to five carbon atoms.

6. Process of manufacturing nitroparaffins according to claim 5, wherein the alkane mixed with propane is ethane.

7. Process of manufacturing nitroparaffins according to claim 1 wherein the mixture to be nitrated contains a compound that can release an $NO_2$ group, halogen or free radicals.

8. Process of manufacturing nitroparaffins according to claim 7 wherein said compound is a chloronitroparaffin containing from 1 to 4 carbon atoms.

9. Process of manufacturing nitroparaffins according to claim 1 or 5 wherein the mixture to be nitrated further contains an inert gas.

10. Process of manufacturing nitroparaffins according to claim 9 wherein said inert gas is nitrogen, carbon monoxide, or carbon dioxide.

11. Process of manufacturing nitroparaffins according to claim 1 wherein said nitration is carried out in the presence of an oxygen, the reaction pressure is 10–30 bars, and the contact time is 5–8 seconds.

12. Process of manufacturing nitroparaffins according to claim 1, wherein the reaction temperature is 280°–500° C., the contact time is between 0.01 and 20 seconds, and the reaction pressure is up to 100 bars.

* * * * *